US009216278B2

(12) United States Patent
Heinz et al.

(10) Patent No.: US 9,216,278 B2
(45) Date of Patent: Dec. 22, 2015

(54) LUER LOCK CONNECTION

(75) Inventors: Jochen Heinz, Flintbek (DE); Dieter Schilling, Aukrug-Innien (DE); Ralf Lucyga, Schierensee (DE)

(73) Assignee: Transcoject GmbH, Neumuenster (DE)

( * ) Notice: Subject to any disclaimer, the term of this patent is extended or adjusted under 35 U.S.C. 154(b) by 457 days.

(21) Appl. No.: 13/318,093

(22) PCT Filed: Apr. 27, 2010

(86) PCT No.: PCT/DE2010/000478
§ 371 (c)(1),
(2), (4) Date: Jan. 13, 2012

(87) PCT Pub. No.: WO2010/124676
PCT Pub. Date: Nov. 4, 2010

(65) Prior Publication Data
US 2012/0116355 A1 May 10, 2012

(30) Foreign Application Priority Data
Apr. 30, 2009 (DE) .......................... 10 2009 019 340

(51) Int. Cl.
*A61M 25/16* (2006.01)
*A61M 39/10* (2006.01)
*A61M 5/34* (2006.01)

(52) U.S. Cl.
CPC .......... *A61M 39/1011* (2013.01); *A61M 5/347* (2013.01); *A61M 2039/1016* (2013.01); *A61M 2039/1077* (2013.01)

(58) Field of Classification Search
CPC ..... A61M 5/347; A61M 5/344; A61M 5/346; A61M 5/32; A61M 5/34; A61M 39/1011; A61M 39/10; A61M 39/12; A61M 39/1027; A61M 39/1033; A61M 39/1077; A61M 25/0014; A61B 19/22; A61B 19/2203; A61B 2019/2242; A61B 17/00234; A61B 17/29
USPC ...................... 604/241, 533, 535, 285; 606/1; 220/601, 200
See application file for complete search history.

(56) References Cited

U.S. PATENT DOCUMENTS

| 4,266,815 | A | * | 5/1981 | Cross | 285/330 |
|---|---|---|---|---|---|
| 5,047,021 | A | | 9/1991 | Utterberg | |
| 5,984,373 | A | | 11/1999 | Fitoussi et al. | |
| 6,152,913 | A | | 11/2000 | Feith et al. | |
| 6,508,810 | B1 | * | 1/2003 | Ouchi et al. | 606/1 |

(Continued)

FOREIGN PATENT DOCUMENTS

| DE | 20 2004 012 714 | 12/2004 |
|---|---|---|
| EP | 0 869 826 | 10/1998 |

(Continued)

*Primary Examiner* — Emily Schmidt
*Assistant Examiner* — William Frehe
(74) *Attorney, Agent, or Firm* — Cozen O'Connor

(57) ABSTRACT

The invention relates to a Luer lock connection comprising a Luer cone and a threaded sleeve surrounding said cone, the threaded sleeve being fitted on the base of the Luer cone so that it is rotatable along the longitudinal axis of said cone, wherein clamping means are provided between the threaded sleeve and the base of the Luer cone, said means being designed in such a way that when a female part is fitted onto the Luer cone, clamping between the threaded sleeve and the base of the Luer cone is achieved by rotating the threaded sleeve or the female part in the threaded sleeve (4).

7 Claims, 7 Drawing Sheets

(56) References Cited

U.S. PATENT DOCUMENTS 6,969,375 B2 * 11/2005 Thibault et al. ............... 604/241
7,472,932 B2    1/2009 Weber et al.

FOREIGN PATENT DOCUMENTS

| FR | 2 809 316 | 11/2001 |
| WO | WO 96/33762 | 10/1996 |

* cited by examiner

LUER LOCK CONNECTION

CROSS REFERENCE TO RELATED APPLICATION

This is a U.S. national stage of application No. PCT/DE2010/000478, filed on 27 Apr. 2010. Priority is claimed on German, Application No.: 10 2009 019 340.5, filed: 30 Apr. 2009, the content of which are incorporated here by reference.

FIELD OF THE INVENTION

The invention relates to a Luer lock connection.

BACKGROUND OF THE INVENTION

Luer lock connections are known, with which the threaded sleeve surrounding the Luer cone is rotatable relative to the Luer cone about its longitudinal axis. This design may be intended and e.g. used, to be able to fix a female counter-piece on the Luer cone by rotating the threaded sleeve, without having to rotate the Luer cone. A rotation of the threaded sleeve may be unavoidable if the Luer cone and the threaded sleeve consist of different materials and are put or stuck onto one another, as is common e.g. with glass syringes.

The problem with this design is that the connection may easily come undone, in particular if moisture or lubricant such as e.g. silicone oil gets onto the Luer cone or into the thread of the threaded sleeve, or particularly smooth materials such as e.g. PTFE are used.

SUMMARY OF THE INVENTION

It is an object of the invention to improve a Luer lock connection with a threaded sleeve that is not connected in a fixed manner to the Luer cone, to the extent that the connection of this Luer lock connection to a female counter-piece is secured against unintended detachment.

The Luer lock connection according one embodiment of to the invention comprises a Luer cone and a threaded sleeve surrounding this. Thereby, the threaded sleeve is attached on the end that is away from the free end of the Luer cone, which is to say on the foot of the Luer cone. For this, the threaded sleeve may comprise a radially inwardly projecting projection which engages into an annular groove on the outer periphery of the foot of the Luer cone. Thus the threaded sleeve may be rotated about the Luer cone about its longitudinal axis. Thereby, for example, the radially inwardly directed projection of the threaded sleeve may slide in the groove in the peripheral direction. The groove and the projection thereby form an axial locking which limits or prevents the axial movability of the threaded sleeve in the direction of the longitudinal axis of the Luer cone.

According to one embodiment of the invention, additional clamping elements are provided between the threaded sleeve and the foot of the Luer cone, and these clamping elements form a rotation lock when a female counter-piece is put onto the Luer cone or is screwed into the threaded sleeve. By way of these clamping elements, the threaded sleeve is then prevented from being able to rotate in an unintended manner, in particular on its own, for example by way of external shakings, whereby such a rotation would lead to a loosening of the connection between the Luer lock connection and the female counter-piece. The clamping elements are designed in a manner such that when a female counter-piece is put onto the Luer cone, they achieve a clamping between the threaded sleeve and the foot of the Luer cone by way of rotating the threaded sleeve or rotating the female counter-piece in the threaded sleeve. An additional securing or locking of the connection is achieved by way of this clamping. With conventional Luer lock connections, a locking between the conical outer surface of the Luer cone and the female counter-piece is achieved due to friction. Additionally, an axial locking is secured by way of the thread of the threaded sleeve. With conventional Luer lock connections, the threaded sleeve is however held in the thread merely by way of the friction. According to one embodiment of the invention, by way of the clamping elements, an additional friction-fit and/or positive-fit connection or clamping is now created directly between the threaded sleeve and its mounting at the foot of the Luer cone. The clamping elements, preferably directly on the threaded sleeve and/or on the foot of the Luer cone, are designed such that for additional securing, a positive-fit and non-positive fit engagement is effected between the threaded sleeve and the foot of the Luer cone, for rotational locking i.e. the clamping elements form engagement elements acting with a positive fit and non-positive fit. By way of this additional locking, one may create a secure retention, in particular also if moisture or lubricant should get onto the thread or the Luer cone. Since the clamping means according to the invention moreover are arranged in the foot region of the Luer cone, i.e. at the end which is away from the free end of the Luer cone, one may prevent humidity which exits from the Luer lock connection, for example with pre-filled cartridges, from getting in the region of the clamping means.

Advantageously, the clamping elements comprise at least one contact surface at the foot of the Luer cone and a counter-contact surface on the threaded sleeve arranged in a manner such that with a female counter-piece put onto the Luer cone, they engage with one another by way of relative rotation between the threaded sleeve and the female counter-piece. The relative rotation between the threaded sleeve and the female counter-piece may be effected by way of rotation of the threaded sleeve and/or of the female counter-piece. The threaded sleeve is preferably freely rotatable as long as the female counter-piece is not put on. Thus the threaded sleeve in the known manner may be screwed onto the thread of a female counter-piece and thus the female counter-piece may be pulled over the threaded sleeve onto the Luer cone. The contact surface and counter-contact surface are arranged or designed such that they only come into frictional contact or in engagement when the female counter-piece is clamped on the Luer cone. In this manner, a free rotatablity of the threaded sleeve is achieved until the firm bearing contact of the female counter-piece on the Luer cone and only then is the additional clamping between the contact surface and counter-contact surface achieved as a rotational lock of the threaded sleeve.

Further preferably, the threaded sleeve is held at the foot of the Luer cone with play which is dimensioned such that it is eliminated by way of the engagement of the female counter-piece with the Luer cone and the threaded sleeve, by which the contact surface and the counter-contact surface engage with one another. It may thereby be the case of an axial and/or radial play with respect to the longitudinal axis of the Luer cone. This play ensures the free rotatablity of the threaded sleeve as long as the female counter-piece is not put onto the Luer cone. Only then, by way of screwing the threaded sleeve onto the thread of the female counter-piece and/or screwing of the female counter-piece into the threaded sleeve, is the play eliminated either in the axial and/or radial direction, by way of the movement of the threaded sleeve relative to the foot of the Luer cone, so that the contact surfaces and the counter-contact surfaces come into engagement with one another.

The arrangement of additional clamping means according to the invention may however not only be applied in the case, in which a rotatablity between the threaded sleeve and the Luer lock connection is desired for screwing onto the female counter-piece. Luer lock connections are also known, with which the threaded sleeve is actually not designed in a rotatable manner, but a rotation may not be completely prevented on account of the material pairing between the Luer cone and the threaded sleeve. This may be the case with glass syringes for example, with which a threaded sleeve of plastic is put onto a Luer cone or its foot of glass. With these Luer lock connections too, the additional clamping elements may be applied, in order to prevent a rotation of the threaded sleeve when the connection between the female counter-piece and the Luer lock connection with the Luer cone is created. With this design, the relative rotation between the threaded sleeve and the female counter-piece, which causes the clamping of the clamping elements, is preferably achieved by way of rotating the female counter-piece in the threaded sleeve.

According to one further embodiment of the invention, the contact surface and/or the counter-contact surface has a profiled surface. The profiled or structured surface may serve for increasing the friction between the contact surface and the counter-contact surface. Moreover, also both surfaces may be profiled in a manner such that a positive-fit engagement between the contact surface and the counter-contact surface occurs. For example, the contact surface and the counter-contact surface may each be designed in a toothed manner, so that the teeth engage or mesh with one another with a positive fit, and form a rotation lock. Such a profiled, in particular toothed structure may thereby be designed such that a release of the connection is possible. This is effected by way of an increased torque being applied onto the threaded sleeve or onto the screwed-in female counter-piece, by way of which torque the friction between the contact surface and counter-contact surface is overcome. Thereby, the friction or clamping of the clamping elements, in particular in the form of a contact surface and a counter-contact surface, is selected such that the release moment is so high, that the connection may not be released in an unintended manner, for example by way of external shaking. Moreover, it is possible to design the clamping such that is not reversible without destruction, by way of suitable profiling or toothing of the contact surface and the counter-contact surface. For this, teeth for example with flanks which are steep on one side or with undercuts may be provided, so that the teeth act as blocking pawls.

According to a further preferred embodiment, the contact surface and/or the counter-contact surface are designed in an annular, in particular circularly annular manner. Thereby, the counter-contact surface may annularly encompass the contact surface. The contact surface and/or counter-contact surface may thereby be parts of the guiding of the threaded sleeve on the foot of the Luer cone. This means that the contact surface may be part of a groove on the foot of the Luer cone, for example the groove base or one of the groove walls. The counter-contact surface may thereby be a corresponding annular inner surface or one of the axial end-sides of a radially inwardly directed projection of the threaded sleeve which engages into the previously described groove. By way of the annular design of the contact surface and/or of the counter-contact surface, one may succeed in a clamping being achieved at any angular position between the Luer cone and the threaded sleeve. This is particularly advantageous, since usually the female counter-piece may be put onto the Luer cone also at any angular position with respect to the longitudinal axis of the Luer cone.

The contact surface at the foot of the Luer cone may preferably be designed in a conical manner, wherein the conical contact surface tapers in the opposite direction to the Luer cone. This means that the Luer cone widens in its diameter in the known manner from its free end to the foot of the Luer cone. Then, additionally, a contact surface which tapers in the reverse direction, is formed on the foot of the Luer cone, for example in the inside of a groove for receiving a radial projection of the threaded sleeve. This means that the contact surface has the largest diameter at its end which faces the free end of the Luer cone. By way of this design, one may succeed in a counter-contact surface or a counter-contact edge of the threaded sleeve being able to come into bearing contact on the conical contact surface in a clamping manner, when a female counter-piece is put onto the Luer cone, and the threaded sleeve is screwed onto the thread of the female counter-piece, or the female counter-piece is screwed into the threaded sleeve. The female counter-piece is pulled or pressed onto the Luer cone by way of screwing the threaded sleeve onto the female counter-piece or screwing-in the female counter-piece. Thereby, simultaneously, an axial counter force is exerted onto the threaded sleeve in the direction of the free end of the Luer cone. This force is utilised, to press the counter-contact surface against the conical contact surface, so that an additional clamping element is created, which prevents the threaded sleeve from rotating at the foot of the Luer cone, due to clamping or friction.

For this, the counter-contact surface is preferably designed in a manner which corresponds conically to the contact surface, i.e. the counter-contact surface is bevelled at the same angle with respect to the longitudinal axis of the Luer cone as the contact surface. The angle lies in a range of 6° which is similar to the angle of the Luer cone. The contact surface and counter-contact surface may contact in a large-surfaced manner by way of the corresponding conical design, so that a large friction between both surfaces and thus preferably a self-locking may be achieved.

Further preferably, the contact surface and the counter-contact surface are arranged concentrically to the longitudinal axis of the Luer cone. In the released condition, this permits the counter-contact surface to be moved in rotation about the contact surface or relative to the contact surface, so that the threaded sleeve may be rotated about the Luer cone.

According to a further preferred embodiment, the counter-contact surface lies radially opposite the contact surface with respect to the longitudinal axis of the Luer-cone. Thus the contact surface may be a cylindrical annular surface that faces outwards and extends around the foot of the Luer cone, for example in a groove for receiving a radial projection of the threaded sleeve. The counter-contact surface may be an annular, cylindrical inwardly facing surface on the threaded sleeve, which thus peripherally surrounds the contact surface. In this manner, one may ensure that the contact surface and the counter-contact surface lie opposite one another at every angular position. However, it is also conceivable for the contact surface or the counter-contact surface not to extend over the whole periphery about the longitudinal axis of the Luer cone, but to merely extend over limited peripheral sections. Thereby, the respective oppositely lying other surface is then preferably designed as a closed ring, so that one continues to ensure that a bearing contact may be achieved at every angular position.

In a further embodiment of the invention, the counter-contact surface with respect to the longitudinal axis of the Luer cone, has a section situated further radially inwards than a second of the contact surface, wherein the threaded sleeve is arranged at the foot of the Luer cone with radial play. Thereby, the radial play is usefully selected such that the threaded sleeve, due to the play, may continue to rotate about the Luer cone in the released condition, i.e. when no female counter-piece is stuck onto the Luer cone. Thereby, the counter-contact surface may pass the contact surface at every location by way of radial movement of the threaded sleeve on account of the play. As described above, the contact surface and the counter-contact surface are however preferably designed such that the radial play is eliminated on inserting the female counter-piece and screwing the threaded sleeve with its thread, so that the contact surface and the counter-contact surface are pressed against one another. Thereby, in particular the section of the counter-contact surface which is situated further radially inwards, comes to bear on the contact surface in a clamping manner.

This may be achieved for example by way of the contact surface and the counter-contact surface being designed in an annular and in particularly annulus-like manner, and the contact surface and/or the counter-contact surface being arranged eccentrically to the longitudinal axis of the Luer cone. Thereby, the play of the threaded sleeve may be selected such that without the inserted female counter-piece, it is possible to displace the threaded sleeve in the radial direction relative to the foot of the Luer cone, such that the axes of the annular contact surface and of the annular counter-contact surface are essentially congruent, so that these may be rotated relative to one another. Thereby, the longitudinal axis of the threaded sleeve is displaced parallel to the longitudinal axis of the Luer cone. The radial play preferably corresponds essentially to the eccentricity or is slightly smaller. Then, the longitudinal axis of the threaded sleeve is centred with the longitudinal axis of the Luer cone by way of inserting the female counter-piece, so that the annular contact surface and the annular counter-contact surface are no longer arranged concentrically, but eccentrically to one another, so that a clamping contact of the contact surface and counter-contact surface occurs in a peripheral section. Specially, this peripheral section, in particular of the contact surface, may furthermore be provided with a profile. Preferably, the contact surface may be designed in an annular manner and comprises a middle or longitudinal axis which is offset parallel to the longitudinal axis of the Luer cone.

Apart from the previously described two examples for the design of the clamping elements, once as a conical contact surface and once as contact surfaces and counter-contact surfaces which are eccentric to one another, one may also envisage alternative other designs, for example wedge surfaces or likewise, which may be brought into clamping bearing contact with one another by way of screwing the threaded sleeve onto the female counter-piece or screwing the female counter-piece into the threaded sleeve.

The design according to the invention is suitable in particular for Luer-lock connections, with which the Luer cone and the threaded sleeve are manufactured from different materials. This may for example be a Luer cone of glass as part of a glass syringe or cartridge, and a threaded sleeve of plastic. Conventionally, a rotationally secure fixation is not always possible with the attachment of the threaded sleeve of plastic on the foot of the Luer cone of glass. This may be ensured at least in the condition connected to the counter-piece, on account of the design according to the invention. Moreover, the design according to the invention is further suitable in particular also with the use of materials with self-lubricating characteristics such as PTFE. With such materials, one may ensure a secure fixation of the threaded sleeve when this is connected to a counter-piece, by way of the additional clamping means.

BRIEF DESCRIPTION OF THE DRAWINGS

The invention is hereinafter described by way of example and by way of the attached figures. In these are shown in:

FIG. 5 is a view of the Luer cone according to FIG. 4 which is sectioned normally to the longitudinal axis, with a threaded sleeve which is put on;

DETAILED DESCRIPTION OF THE PREFERRED EMBODIMENTS

Figure 1:
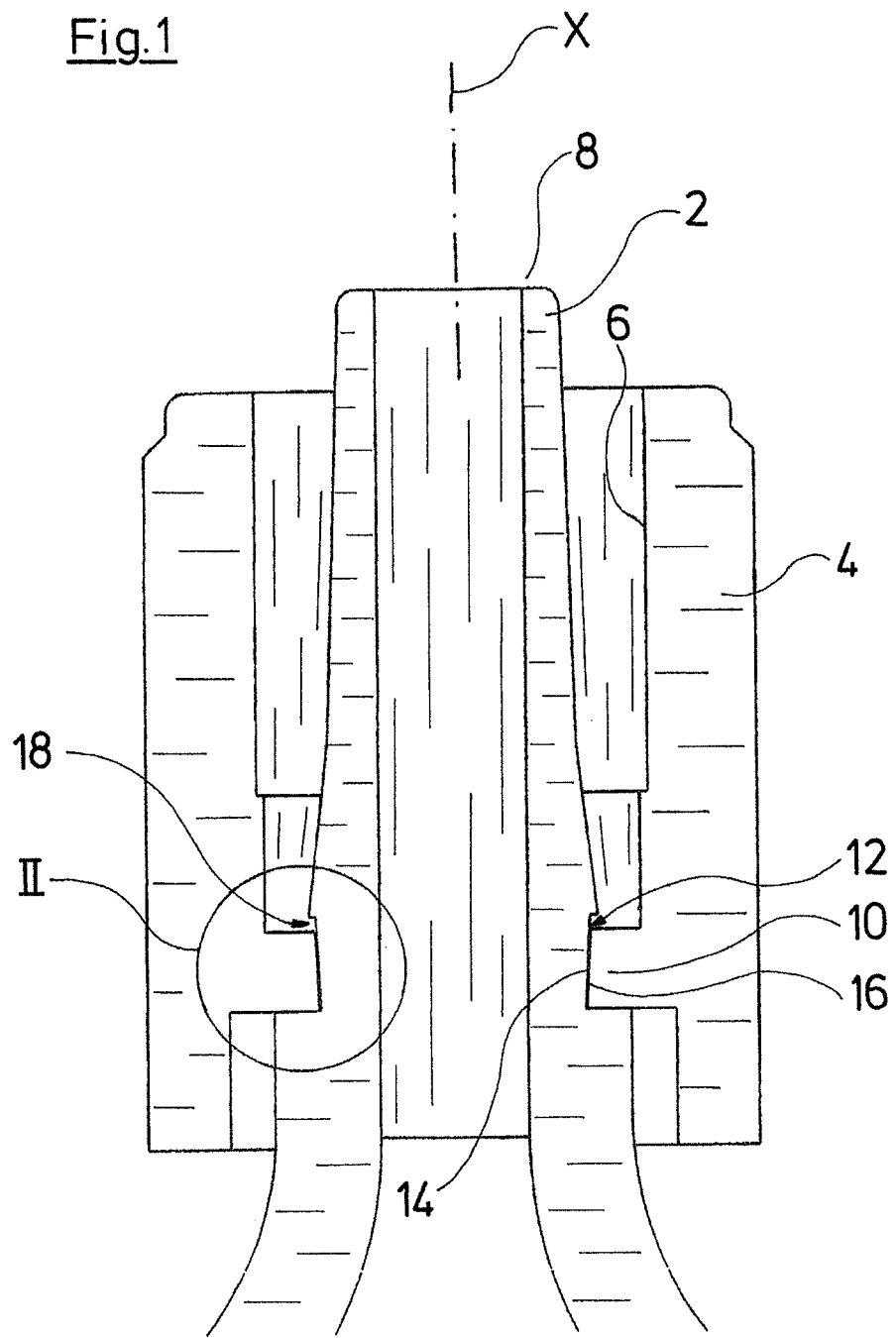
FIG. 1 is a schematic sectioned view of a first embodiment of the invention.

FIG. 1 shows a first embodiment of the Luer lock connection according to the invention, with a Luer cone 2 and with a surrounding threaded sleeve 4 which on its inner peripheral surface 6 carries an inner thread which is not shown here and which is common to Luer lock connections. The threaded sleeve 4 on its end, which is away from the free end 8 of the Luer cone 2, comprises a radially inwardly directed annular projection 10 that engages into an annular groove 12 at the foot of the Luer cone 2. In this manner, the threaded sleeve 4 is rotatable in the known manner about the longitudinal axis X of the Luer cone 2 relative to the Luer cone 2, but is secured in the axial direction X. Thus the threaded sleeve 4 with its inner thread, which is not shown here, may be screwed onto a corresponding outer thread of a female counter-piece put onto the Luer cone 2, so that the counter-piece is brought into bearing contact with the Luer cone 2.

According to one embodiment of the invention, an additional clamping element is now provided for rotational locking of the threaded sleeve 4 when this is in engagement with a counter-piece which is not shown here. This clamping element is formed by a contact surface 14 and a counter-contact surface 16. The contact surface 14 is formed by the base of the groove 12, whilst the counter-contact surface 16 is formed by the inner peripheral surface of the annular projection 10 on the threaded sleeve 4. The contact surface 14 as well as the counter-contact surface 16 is designed in a conical manner. Thereby, the inclination angle is selected such that the cone tapers in the opposite direction to the Luer cone 2. This means that the axial end of the contact surface 14, which is smaller in diameter and of the counter-contact surface 16, is the end of the contact surface 14 which is away from the free end of the Luer cone 2 and of the counter-contact surface 16 respectively. The inclination angle of the contact surface 14 as well as of the counter-contact surface 16 may correspond essentially to the inclination angle of the Luer cone.

Figure 2:
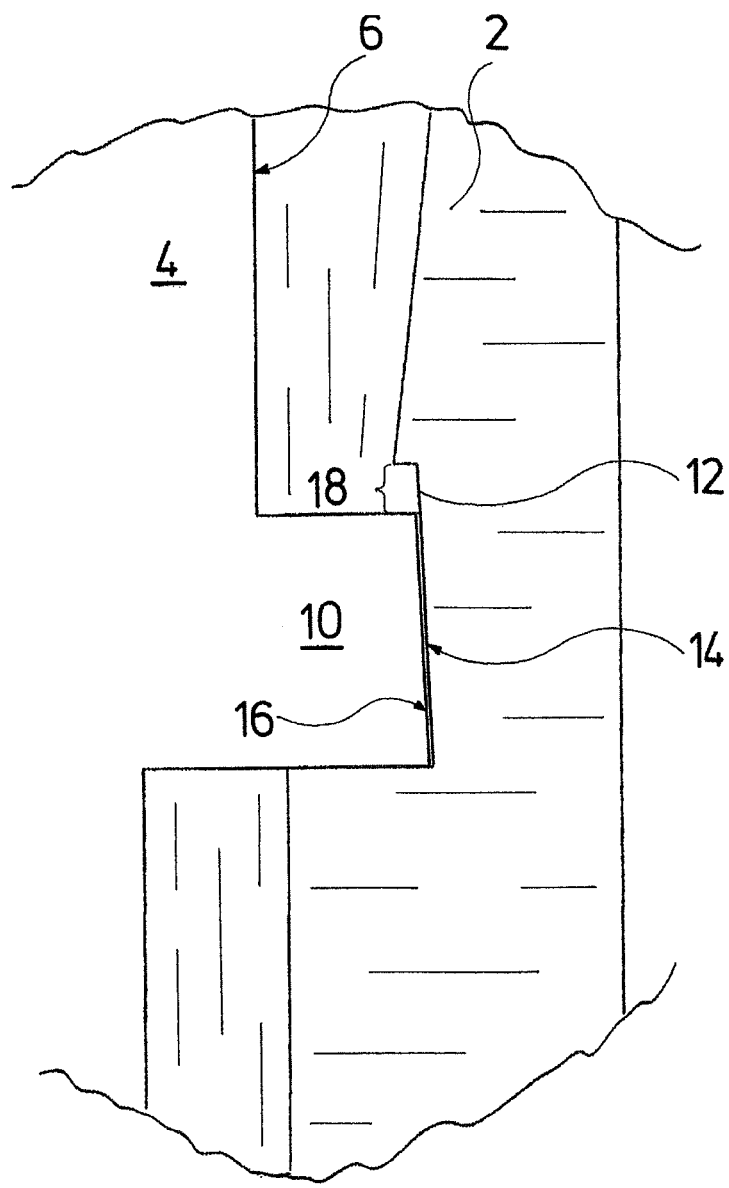
FIG. 2 is an enlargement of the detail II in FIG. 1.

As shown in FIG. 2, the groove 12 in the axial direction X is wider than the projection 10, so that an axial play 18 exists between the threaded sleeve 4 and the Luer cone 2. In the released condition which is shown in FIGS. 1 and 2, the threaded sleeve 4 may thus be moved slightly to the rear from the free end 8 of the Luer cone 2, so that the contact surface 14 and the counter-contact surface 16 are not in clamping or sticking bearing contact with one another, as is shown in FIG. 2. This permits the threaded sleeve 4 to be freely rotated about the Luer cone 2. If now a female counter-piece is placed on the Luer cone 2, and with whose outer thread the inner thread of the threaded sleeve 4 comes into engagement, the female counter-piece is pressed onto the Luer cone 2 in the axial direction, by which simultaneously the threaded sleeve 4 is pressed or displaced in the direction of the free end 8 of the Luer cone 2. By way of this, the contact surface 14 and the counter-contact surface 16 come into bearing contact with one another, so that these are pressed against one another. An additional friction or an additional clamping between the contact surface 14 and the counter-contact surface 16 is created in this manner and this clamping prevents a rotation of the threaded sleeve 4 about the longitudinal axis X. To rotate the threaded sleeve 4 about the longitudinal axis X, for example for releasing the connection, an increased torque must be applied, in order to overcome the friction between the contact surface 14 and the counter-contact surface 16. This increased moment may be so large, that an unintended release, for example due to shaking, may be reliably prevented. According to one embodiment of the invention, thus an additional clamping is created in a direct manner between the Luer cone 2 or the foot of the Luer cone 2 and the threaded sleeve 4, which secures the threaded sleeve 4 from rotating in the condition connected to a counter-piece.

Figure 3:
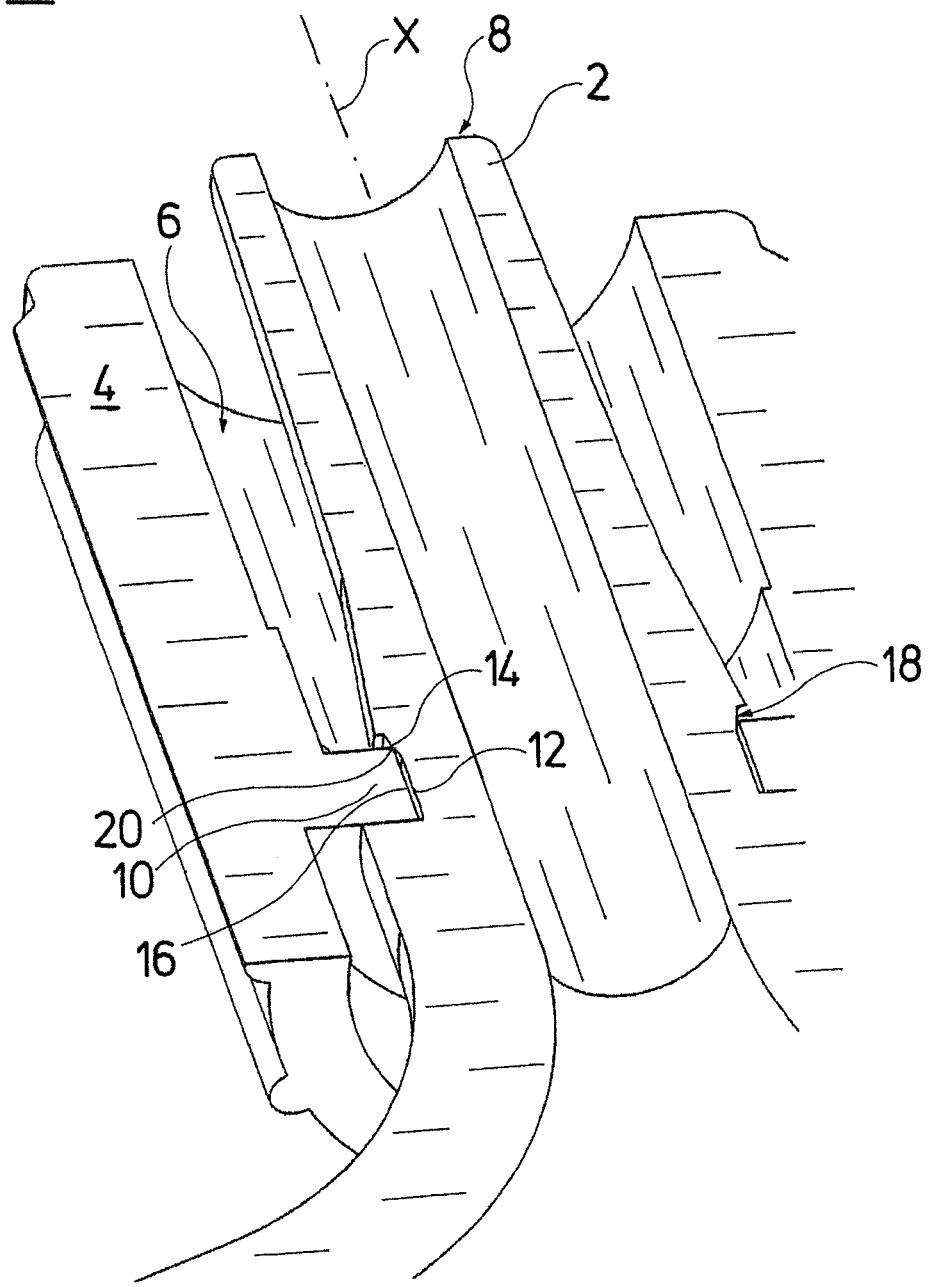
FIG. 3 is a perspective sectioned view of one variation of the embodiment according to FIG. 1.

FIG. 3 shows a variant of the embodiment according to FIGS. 1 and 2. With this embodiment, a conical contact surface 14 is likewise provided in the groove 12, but this does not extend completely over the axial length of the groove base. The conical contact surface 14 with this embodiment is rather situated only at the axial end of the groove 12 which is away from the free end 8 of the Luer cone. Moreover, with this embodiment, no corresponding counter-contact surface 16, which is likewise conical, is envisaged on the projection 10. Here, the counter-contact surface 16 is formed in the shape of a contact line by the front edge 20 of the projection 10, i.e. the edge which faces the free end of the Luer cone 8. This edge 20 in the clamped or connected condition comes to bear on the contact surface 14. A high surface pressing is achieved by way of the linear bearing contact region, so that a firm clamping between the threaded sleeve 4 and the Luer cone 2 for the rotational locking of the threaded sleeve 4 is achieved with this embodiment too. Otherwise, the embodiment according to FIG. 3 corresponds to the previously described embodiment.

With the embodiments according to FIGS. 4 to 7, the clamping between the threaded sleeve 4 and the Luer cone 2 is not achieved in the axial direction, as with the previously described embodiment, but in the radial direction.

Figure 4:
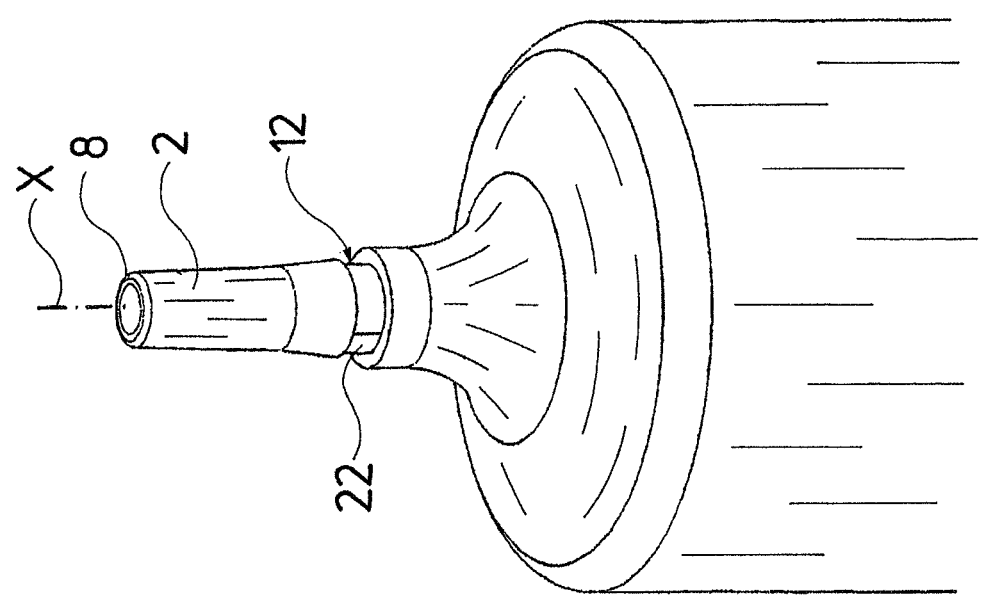
FIG. 4 is a schematic view of the Luer cone according to a second embodiment of the invention.

FIG. 4 shows the Luer cone 2 without a threaded sleeve. With this embodiment too, a groove 12 for receiving a radial projection of the threaded sleeve is provided on the foot of the Luer cone 2 which is away from the free end 8. With this embodiment, the groove base 22 also forms a contact surface as part of a clamping element. The contact surface 22 is designed in an annulus-like manner, but not concentrically to the longitudinal axis X of the Luer cone 2, but eccentrically, so that the longitudinal or middle axis of the annulus-like contact surface 22 is offset parallel to the longitudinal axis X of the Luer cone 2. As is to be recognised in the sectioned view in FIG. 5, with this embodiment too, the threaded sleeve 4 engages with a projection into the groove 12. Thereby, the inner periphery of the projection 12 forms a counter-contact surface 24. The counter-contact surface 24 is likewise designed in an annulus-like manner, i.e. it has the shape of a circular cylinder with a slightly larger diameter than the circularly cylindrical contact surface 22. The counter-contact surface 24 is designed concentrically to the inner surface 6 (see FIG. 1 to 3) of the threaded sleeve 4, on which the inner thread is arranged. i.e., if a female counter-piece is stuck onto the Luer cone 2, the threaded sleeve 4 is centred to the longitudinal axis X of the Luer cone 2 and thus also the counter-contact surfaces 4 to this longitudinal axis X. Since the contact surface 2 is designed eccentrically to the longitudinal axis X of the Luer cone 2, a frictional-fit or clamping bearing-contact between the contact surface 24 and the counter-contact surface 26 occurs in a peripheral section 26. i.e., the counter-contact surface 26 is pressed against the contact surface 24 by way of the centring of the threaded sleeve 4 which is effected when connecting. The peripheral section 26, in which the contact between the contact surface 22 and the counter-contact surface 24 occurs, is thereby that peripheral section, in which the contact surface 22 has its greatest radial distance to the longitudinal axis X of the Luer-cone. The dimensions of the inner diameter of the counter-contact surface 24 and of the contact surface 22 are thereby selected such that in the centered position of the threaded sleeve, the radius of the counter-contact surface 24 is ideally at least slightly smaller than the largest radial distance of the contact surface 22 to the longitudinal axis X of the Luer cone 2. A secure clamping is achieved in this manner.

Figure 5:
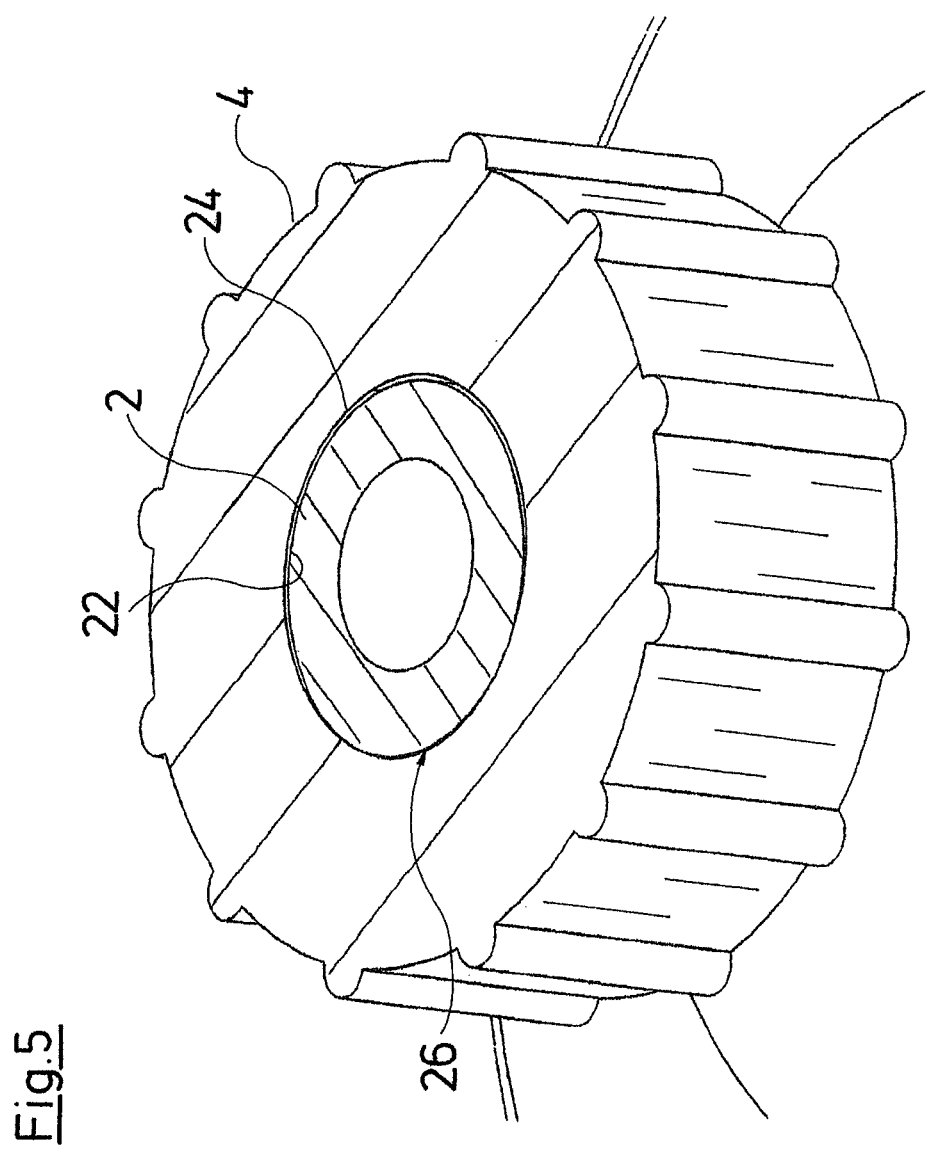
Figure 6:
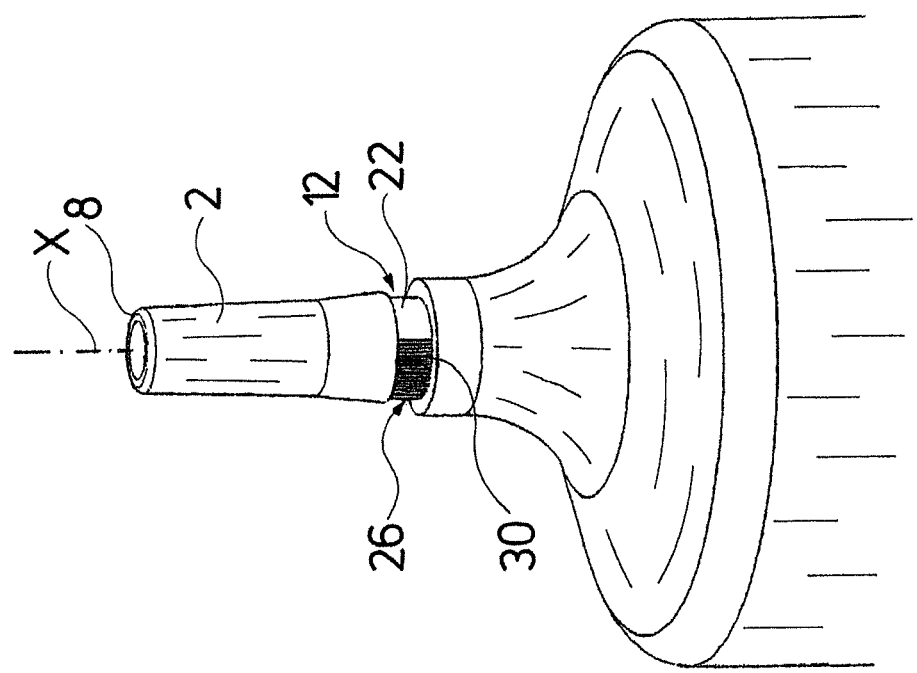
FIG. 6 is a perspective view of a Luer cone according to one variant of the embodiment according to FIG. 4.
Figure 7:
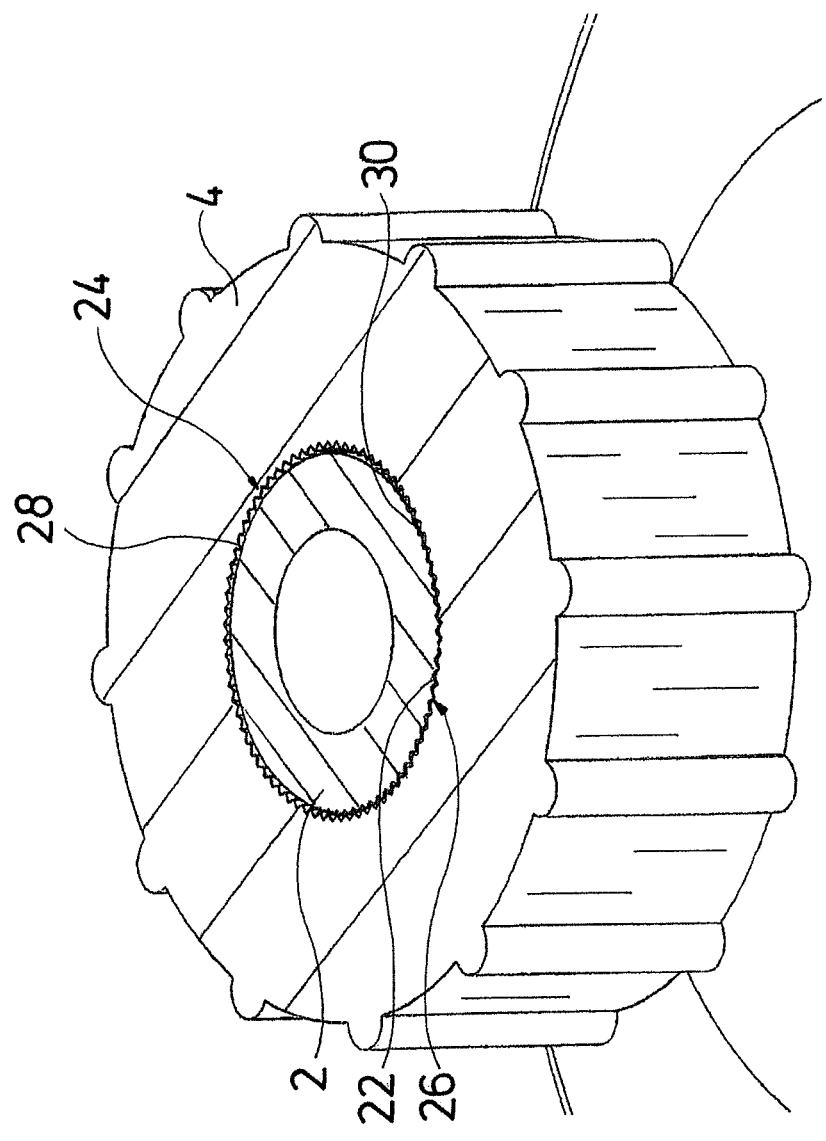
FIG. 7 is a view of the Luer cone according to FIG. 6, which is sectioned normally to the longitudinal axis, with a stuck-on or put-on threaded sleeve.

FIGS. 6 and 7 show a variant of the embodiment according to FIGS. 4 and 5, with which additionally, a profiling of the contact surface 22 and of the counter-contact surface 24 is envisaged in the form of a toothing 28, 30. In this manner, not only is a friction-fit connection, but additionally a positive-fit connection is created in the peripheral section 26, in which the contact surface 22 comes to bear on the counter-contact surface 24. The toothing 28 is arranged over the whole inner periphery of the counter-contact surface 24. In contrast, a corresponding toothing 30 is formed on the contact surface 22 only in the peripheral section 26, in which the contact surface 22 and the counter-contact surface 24 come into engagement. The toothings 28 and 30 correspond to one another, i.e. are designed with essentially the same cross-sectional shape of the teeth, so that the toothings 28 and 30 may come into engagement with one another. Simultaneously, the inner diameter of the counter-contact surface 24 is selected larger than the outer diameter of the contact surface 24, in a mannersuch that the counter-contact surface 24 may be rotated about the contact surface 22 in the released condition, i.e. when the middle axis of the counter-contact surface 24 is offset parallel to the longitudinal axis X of the Luer cone 2. In this manner, one ensures that the threaded sleeve 4 may be rotated freely about the Luer cone 2 in the released condition.

It is to be understood that the contact surfaces 14 and 22 as well as counter-contact surfaces 16 and 24 according to the preceding description may also be profiled in a different manner, in particular the contact surface 14 and/or the counter-contact surface 16 according to the first embodiment may be provided with a profiling or structuring for an additional positive-fit engagement.

With the described embodiment examples, the threaded sleeve 4 is designed in a rotatable manner and the screwing of the female counter-piece and threaded sleeve 4 is effected by way of rotating the threaded sleeve. However, it is to be understood that the described clamping between the threaded sleeve 4 and the foot of the Luer cone is effected in an identical manner, when it is not the threaded sleeve 4 which is rotated, but the female counter-piece for screwing to the threaded sleeve 4.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A Luer lock connection comprising:
a Luer cone;
a threaded sleeve surrounding the Luer cone, the threaded sleeve attached on a foot of the Luer cone in a rotatable manner about a longitudinal axis of the Luer cone;
a clamping element provided between the threaded sleeve and the foot of the Luer cone,
wherein the clamping element comprises at least one contact surface on the foot of the Luer cone and a counter-contact surface arranged radially opposite the contact surface with respect to a longitudinal axis of the Luer cone on the threaded sleeve arranged such that with the female counter-piece on the Luer cone the at least one contact surface and the counter-contact surface come into a positive-fit engagement with one another by one of rotation of one of the threaded sleeve and rotation of the female counter-piece in the threaded sleeve,
wherein at least one of the contact surface and the counter-contact surface is designed in an annular manner,
wherein one of the contact surface and the counter-contact surface is arranged eccentrically to the longitudinal axis of the Luer cone,
wherein, with respect to the longitudinal axis of the Luer cone, the counter-contact surface has a first section situated radially further inwards than a second section of the contact surface, and
wherein the threaded sleeve is arranged on the foot of the Luer cone with radial play,
wherein at least one of the contact surface and the counter-contact surface has a profiled surface, and
wherein the contact surface is conical at the foot of the Luer cone and tapers in an opposite direction to the Luer cone.

2. The Luer lock connection according to claim 1, wherein the counter-contact surface is designed conically with respect to the contact surface.

3. The Luer lock connection according to claim 2, wherein the contact surface and the counter-contact surface are arranged concentrically with respect to a longitudinal axis of the Luer cone.

4. The Luer lock connection according to claim 1, wherein the threaded sleeve is retained on the foot of the Luer cone with play and is dimensioned such that the play is eliminated by engagement of the female counter-piece with the Luer cone and the threaded sleeve, by which the contact surface and the counter-contact surface come into engagement with one another.

5. The Luer lock connection according to claim 1, wherein the contact surface and the counter-contact surface are annular.

6. The Luer lock connection according to claim 1, wherein the Luer cone and the threaded sleeve are different materials.

7. The Luer lock connection according to claim 1, wherein the contact surface and the counter-contact surface have teeth that engage with one another with the positive fit.

\* \* \* \* \*